(12) United States Patent
Svadil et al.

(10) Patent No.: US 7,048,787 B2
(45) Date of Patent: May 23, 2006

(54) AIR CLEANER

(76) Inventors: Ragne Svadil, Träådgardsgatan 22, S-172 38 Sundbyberg (SE); Ove Wihk, Virebergsvägen 26, S-171 40 Solna (SE)

( * ) Notice: Subject to any disclaimer, the term of this patent is extended or adjusted under 35 U.S.C. 154(b) by 68 days.

(21) Appl. No.: 10/483,644

(22) PCT Filed: Jul. 11, 2002

(86) PCT No.: PCT/SE02/01375

§ 371 (c)(1),
(2), (4) Date: Jan. 13, 2004

(87) PCT Pub. No.: WO03/009944

PCT Pub. Date: Feb. 6, 2003

(65) Prior Publication Data

US 2004/0168573 A1    Sep. 2, 2004

(30) Foreign Application Priority Data

Jul. 16, 2001    (SE) .................................... 0102539

(51) Int. Cl.
*B03C 3/41*    (2006.01)
*B03C 3/49*    (2006.01)
(52) U.S. Cl. .......................... 96/97; 55/DIG. 38; 96/98
(58) Field of Classification Search ............. 96/95–97, 96/80–82, 98–100; 55/DIG. 38
See application file for complete search history.

(56) References Cited

U.S. PATENT DOCUMENTS

| | | | | |
|---|---|---|---|---|
| 1,322,163 A | * | 11/1919 | Conover | 96/97 |
| 1,381,719 A | * | 6/1921 | McGee et al. | 95/69 |
| 2,244,279 A | * | 6/1941 | White | 96/96 |
| 2,484,202 A | * | 10/1949 | Wintermute | 73/28.04 |
| 3,879,986 A | * | 4/1975 | Sehmel | 73/28.04 |
| 4,202,674 A | * | 5/1980 | Rodenberger et al. | 96/63 |
| 4,352,681 A | * | 10/1982 | Dietz | 96/61 |
| 4,390,426 A | * | 6/1983 | Vicard | 210/243 |
| 4,496,375 A | | 1/1985 | Le Vantine | 96/66 |
| 4,588,423 A | * | 5/1986 | Gillingham et al. | 96/43 |
| 4,689,951 A | * | 9/1987 | Polach | 60/275 |
| 5,055,115 A | * | 10/1991 | Yikai et al. | 96/59 |
| 5,484,472 A | * | 1/1996 | Weinberg | 96/26 |
| 5,518,531 A | * | 5/1996 | Joannu | 96/55 |
| 5,538,692 A | * | 7/1996 | Joannou | 422/121 |
| 5,925,170 A | * | 7/1999 | Nojima | 96/71 |

(Continued)

FOREIGN PATENT DOCUMENTS

DE    3234200    * 3/1983    .................... 96/96

(Continued)

OTHER PUBLICATIONS

International Search Report, PCT/SE02/01375, Nov. 1, 2002.

*Primary Examiner*—Richard L. Chiesa
(74) *Attorney, Agent, or Firm*—Ostrolenk, Faber, Gerb & Soffen, LLP

(57) ABSTRACT

An air cleaner has an electron generator that includes a pointed head, a collector element and an electric circuit included in the electron generator for generating a negative potential on the pointed head and a positive potential on the collector element. The pointed head is mounted at the free end of a cylinder of electrically non-conductive insulating material. The cylinder includes the electric circuit at the free end whereas its other end enters the collector element, which is cylindrical and is of electrically conductive material.

1 Claim, 1 Drawing Sheet

U.S. PATENT DOCUMENTS

| | | | |
|---|---|---|---|
| 5,958,112 A * | 9/1999 | Nojima | 96/55 |
| 6,042,637 A * | 3/2000 | Weinberg | 96/58 |
| 6,506,238 B1 * | 1/2003 | Endo | 96/79 |
| 6,620,224 B1 * | 9/2003 | Sato | 96/83 |
| 6,635,105 B1 * | 10/2003 | Ahlborn et al. | 96/28 |

FOREIGN PATENT DOCUMENTS

| | | |
|---|---|---|
| EP | 0 281 414 | 9/1988 |
| SE | 512 282 | 2/2000 |

\* cited by examiner

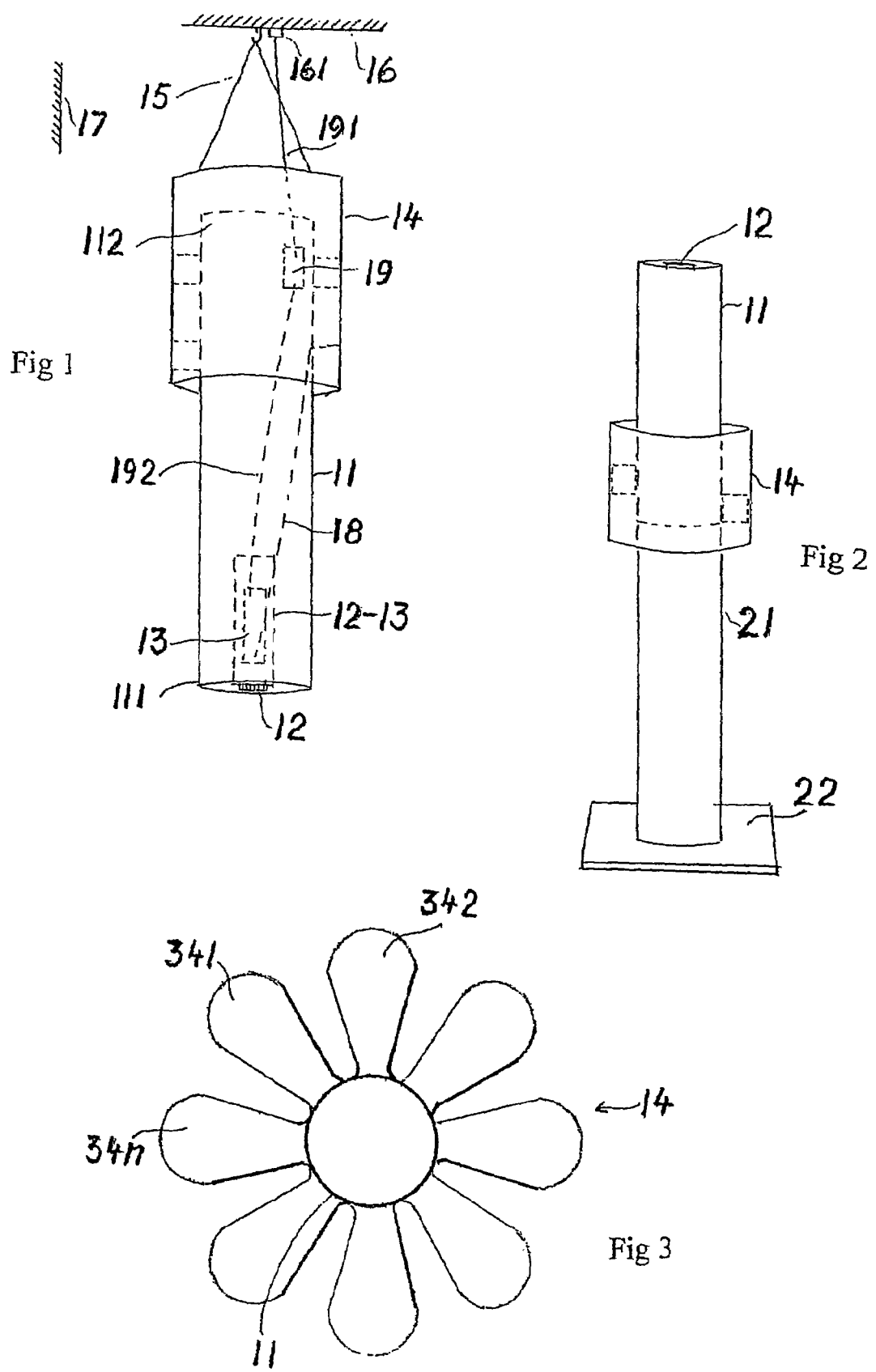

AIR CLEANER

CROSS REFERENCE TO RELATED APPLICATION

The present application is a 35 U.S.C. 00 371 national phase conversion of PCT/SE02/01375, filed 11 Jul. 2002, which claims priority of Swedish Application No. 0102539-4, filed 16 Jul. 2001. The PCT International Application was published in the English language.

TECHNICAL FIELD

The present invention relates to an electronic air cleaner of the kind that includes an electron generator that has a pointed head, a collector element, and an electric circuit included in the electron generator for generating a negative potential on the pointed head and a positive potential on the collector element.

DESCRIPTION OF THE BACKGROUND ART

An air cleaner of the aforesaid kind is apparent, for instance, from Swedish Patent Specification 512 282. In the case of the air cleaner illustrated in this prior publication, the pointed head is disposed so as to point out towards the center of the space in which air shall be cleaned. Moreover, the collector element is comprised of a plate which is positioned so that the pointed head will be directed away from the plate, which has a surface area of at least 150 cm$^2$ and a convex shape as seen from the pointed head.

Although this air cleaner has been found to fulfil high demands on the cleaning of air in a space, in practice, customers have found it somewhat difficult to position the cleaner in rooms of different kinds and configurations as a result of its design. One object of the present invention is to eliminate this drawback.

SUMMARY OF THE INVENTION

According to the present invention, the pointed head of an air cleaner of the aforedescribed kind is mounted on the free end of a cylinder comprised of electrically non-conducting material, wherein the cylinder includes the electric circuit and the collector element is included in its remaining end, the element being cylindrical in shape and comprised of electrically conductive material.

BRIEF DESCRIPTION OF THE DRAWINGS

The invention will now be described in more detail with reference to the accompanying drawing, which illustrates examples of embodiments according to the invention, wherein FIG. 1 illustrates an embodiment for suspension from a ceiling;

FIG. 2 illustrates an embodiment for placement on a table or floor; and

FIG. 3 is a view from above of an alternative embodiment of a collector included in an inventive air cleaner.

DESCRIPTION OF A PREFERRED EMBODIMENTS

The air cleaner illustrated in FIG. 1 includes an electron generator 12–13 that has a pointed head 12, a collector element 14, and an electric circuit 14 included in the electron generator 12–13 for generating a negative potential on the pointed head 12, via a short conductor, and a positive potential on the collector element 14, via a conductor 18.

The pointed head 12, which is comprised of corona points (carbon fiber bristles), (alternatively special steel needles), is mounted on the free end 111 of a cylinder 11 comprised of an insulating material, e.g. ABS plastic. The cylinder 11 includes the electric circuit 13 at one end thereof whereas the other end 112 extends fully or partially through the collector element 14, which is cylindrical and open both at its top and bottom and comprised of electrically conductive material, e.g. aluminum. In the illustrated embodiment, the collector element 14 has an all-round and double-sided collector function (inwards and outwards). The cylinder 11 is held centered in the collector element 14 by means of spacers on the inner wall of the collector element. (By cylindrical is not necessarily meant a circular-cylinder, but a shape that occurs when a straight generatrix is displaced parallel along a closed path).

The air cleaner can be hung by a suspension device 15 from a ceiling 16 for example, alternatively with a line fastened in the cylinder 112. The shortest distance to the ceiling 16 and to a wall 17 should be at least 20 cm. The distance between the collector element 14 and the pointed head 12 will preferably be at least 12 cm and at most 300 cm.

The air cleaner may be powered from the mains (220 volts) via a ceiling-mounted electric fitting 161 and conductor 191 leading to an adapter (transformer) 19, (alternatively fastened to the ceiling or to a fixed mains connection in the wall), which converts the mains voltage to a low-voltage DC voltage (12 volts). This is delivered via a conductor 192 to the electron generator 12–13, which produces an extremely high DC voltage of very low current, about 5 pA.

The air cleaner illustrated in FIG. 2 is principally of the same construction as that shown in FIG. 1, comprising cylinder 11, pointed head 12 and collector element 14. However, the components are placed in reverse in this case, so that the pointed head 12 faces upwards. Furthermore, the air cleaner includes a foot 21–22, which can be placed freely on a floor (or a table). The foot 21–22 consists of an outwardly extended plastic part 21 of the cylinder 11 and an iron foot plate 22 (alternatively a foot plate comprised of acrylic resin) fastened to the lower end of the part 21.

The alternative embodiment of the collector 14 shown from above in FIG. 3 includes a number of mutually identical bulges 341, 342, . . . 34n around the cylinder 11. These bulges have softly or gently rounded transitions so as to avoid the point effect.

The described inventive air cleaner differs from other, conventional air cleaners by virtue of the following properties, among other things:

as an electronic air cleaner/ioniser; does not create static fields;

functions in the absence of movable parts (e.g. fans/blowers);

also collects ultrafine particles (smaller than 0.1 mμ)/?/ in the absence of expensive filters; and is energy-lean, silent and draught-free.

What is claimed is:

1. An air cleaner comprising
   an electron generator that includes a pointed head,
   a collector element, which is cylindrical and is comprised of electrically conductive material,
   an electric circuit included in the electron generator and operative for generating a negative potential on the pointed head and a positive potential on the collector element, a cylinder comprised of electrically non-conductive insulating material and having a free end; the pointed head is mounted at the free end of the cylinder; the cylinder includes the electric circuit located at the same end as the free end, and the cylinder has another end that passes into the collector element.

* * * * *